March 13, 1973 O. RIEGER Plant Pat. 3,320
BEGONIA PLANT
Filed June 30, 1971
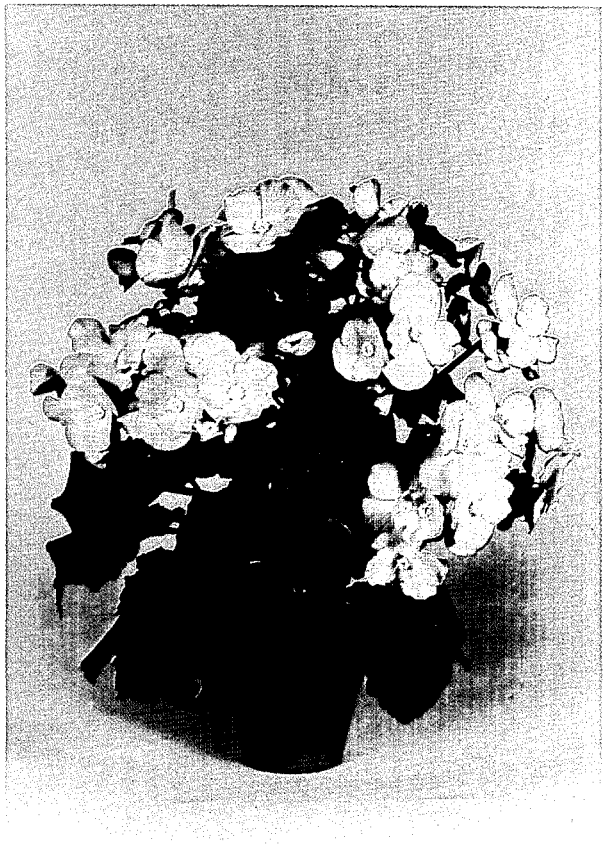

United States Patent Office

Plant Pat. 3,320

Patented Mar. 13, 1973

3,320
BEGONIA PLANT

Otto Rieger, deceased, by Gertrud Rieger, Legal representative, Nurtingen, Germany, assignor to Mikkelsens, Inc., Ashtabula, Ohio Filed June 30, 1971, Ser. No. 158,640
Int. Cl. A01h 5/00
U.S. Cl. Plt.—68 1 Claim The present invention relates to a new and distinctive variety of begonia plant botanically known as *Begonia elatior* resulting from crossing certain begonia selections in a program of hybridization in nurseries at Nurtingen, Germany. The seed parent is an unnamed, unpatented *Begonia tuberhybrida* and the pollen parent is an unnamed unpatented *Begonia socotrana*.

The new cultivar overcomes many drawbacks of previously commercially produced begonia cultivars. Distinguishing characteristics of the new hybrid that are of significant importance to the floricultural industry are as follows:

(1) Extremely good keeping qualities of the flowers. Under conditions of European homes it is not uncommon to have flowers intact 8 to 12 weeks or longer.

(2) Bright orange-red flowers with dominant yellow eyes that are strikingly appealing. Flowers are nearly always male.

(3) In comparison to the well-known Lorraine type of begonia, the new hybrid has flowers larger in size, measuring 5–6 cm. in diameter.

(4) Flowering of this new hybrid can be controlled by manipulation of daylength and temperatures, to a greater extent than on existing varieties. This allows for a greater economic usefulness of the variety.

(5) The overall growth of this variety is more vigorous, stronger, and upright than existing commercial cultivars of this type. Little, if any, staking support is needed to produce good commercial plants.

(6) Outstanding quality plants are produced under the poor growing conditions of northern Europe. This is of economic importance. Spring flowering through May is of superior quality, making a fine addition to Mothers Day pot plants.

(7) This variety is extremely resistant to common mildew, a familiar disease problem of many existing begonia cultivars. This is a major breakthrough in breeding begonias.

(8) Foliage is above average in size, and has a high waxy gloss. The foliage does not easily damage during normal shipping and handling.

(9) Ease of propagation by leaf cuttings that produce an abundance of rhizomatous shoots, thereby allowing a propagator to rapidly increase young plants from a relatively small amount of mother stock. Rapid self branching also allows for efficient production of terminal cuttings.

My new hybrid is illustrated in the accompanying colored photograph showing a typical commercially grown plant from nurseries in Nurtingen, Germany. Colors of foliage and flowers are as true as reasonably possible in color photographs of this type.

The following detailed description of the new hybrid is based on observations and scrutiny of many plants grown under commercial practices in Nurtingen, Germany. As with most plant materials, the rate of growth, size of foliage, size and texture of flowers, and color intensity of flowers varies considerably with light and temperature conditions. The descriptions are based on normal greenhouse practices unless otherwise noted. Color references are to the Royal Horticultural Society Colour Chart, except where general color terms of ordinary dictionary significance are used.

Parentage: The new cultivar is the result of a controlled pollination of a selected *Begonia tuberhybrida* as a seed parent crossed with *Begonia socotrana* as a pollen parent.

Propagation: Continuous and consecutive asexual propagations by cuttings at Nurtingen, Germany clearly indicate that the new variety asexually reproduces true to type. During the above mentioned propagations it was further determined that the new begonia hybrid was equally capable of being propagated both by leaf cuttings and stem bud cuttings which is significantly important in commercial propagation. Both types of cuttings will root in approximately three weeks at 20° C. under favorable propagation conditions. An additional six to eight weeks is needed for the leaf cuttings to produce visible rhizomatous shoots.

Rooting habit: Rooting is rapid, abundant, and fine textured in loose well aerated composts. Roots are readily damaged by moderate to high nutrient salt levels and extreme in high or low soil moisture levels. Optimum pH requirement is 6.

Plant form: Plants are semidwarf, compact and full as a result of easy, free branching characteristics. When a plant from a leaf cutting is properly manipulated to encourage the development of rhizomatous shoots large and extremely full exhibition type specimens as illustrated can be produced in a minimum amount of time and cost. This is a significant economic characteristic of the new hybrid.

Habit of growth: Vigorous, upright, and rapid as compared to most other commercial begonia varieties of this type. Needs very little, if any, support when grown under a properly controlled relationship of heat and light.

Blooming habits: Flowers are borne on stalks in multiples of three subdividing to form trusses of an indeterminate amount of flowers. Once sexual reproduction has been initiated, flowering is quite free.

Blooming season: The natural flowering season of the new hybrid in Germany is late November to early December. With appropriate greenhouse cultural techniques, this begonia variety can be brought into flower at any season of the year making it of further economic importance. Flowering plants produced particularly from late September through to June can help fulfill the demands for a variety of flowering pot plants in this period.

Foliage: Alternate: average to above average in quantity borne at a close angle to the stem and having the following detailed characteristics:

*Size.*—In comparison to other commercial varieties of this type, the foliage would be classified as being generally large, the general plant condition existing under any given set of environments can greatly alter the size, texture and color tones of the foliage.

*Shape.*—Generally oval pointed with pronounced indentation in the area of the leaf petiole to give an overall heart shape.

*Texture.*—Upper side is leathery with a high polished effect; well finished plants have foliage that has luminescence under reflective light conditions. The under side is smooth and quite reflective as if coated with a film of water.

*Margin.*—Young foliage is quite indented and notched with red edges, as foliage matures the margins become less indented with the pointed ends slightly twisted and notched.

*Color.*—New foliage: upper side 146 A; lower side 146 C. Mature foliage: upper side 139 A; lower side 138 A.

*Disease resistance.*—The foliage is quite resistant to common mildew infections when compared with other begonia cultivars in commercial practices.

Flowers: Borne on pyramidal trusses with several clusters of three to a stem. Stems are short to medium in length with sufficient sturdiness to be upright and self supporting. Bracts are flat and are usually four in number measuring up to 6 cm. in diameter. Occasional doubling of bracts occur with the inner bracts being orange in color. The greater majority of the flowers are male with a distinctive yellow eye made up of a cluster of stamens and anthers.

*Quantity.*—Very floriferous with flower development over a considerable length of time, often three to four months. The plant itself usually deteriorates before flowering actually ceases.

*Buds.*—Are flatly folded and progressively develop as the main flowering stem continues to grow and initiates new flowering parts. The flowering bud closely resemblies the shape of a lima bean but develops into a uniformly symmetrical flower usually with four bracts.

*Petals (bracts).*—Upper side nearly 44A to B, maturing to 34 A; reverse side nearly 42 A.

*Reproductive organs.*—Flowers are predominately male; female flowers when they occur are terminal.

Stamens: are quite profuse and because of their color give definite contrast to the coloring of the bracts. Color 14 A. Pollen: is plentiful when the flowers are protected from botrytis. Color 13 B. Styles/ovaries: As in most begonias the pistils are divided into three segments.

What is claimed:

1. A novel and distinctive hybrid *Begonia elatior* variety characterized particularly by superior durability of the plant and its blooms under normal cultivation practices; the longevity of the blooms; the superior floriferous flowering trait producing bright, vivid orange-red colored bracts with a sharp contrasting yellow eye produced by the abundance of stamens and anthers; an overall larger bloom size; controlled flowering response which allows pot plant producers to flower this variety any season of the year; a vigorous upright growth habit that eliminates the necessity of staking; abundant, large waxy foliage that is resistant to mildew; and its ability to be propagated both by leaf cuttings and stem bud cutings.

No references cited.

ROBERT E. BAGWILL, Primary Examiner